US006854331B2

(12) United States Patent
Omata (10) Patent No.: US 6,854,331 B2
(45) Date of Patent: Feb. 15, 2005

(54) SUBSTANCE CHARACTERISTIC MEASURING METHOD AND SUBSTANCE CHARACTERISTIC MEASURING INSTRUMENT

(75) Inventor: Sadao Omata, Koriyama (JP)

(73) Assignee: Nihon University, Tokyo (JP)

( * ) Notice: Subject to any disclaimer, the term of this patent is extended or adjusted under 35 U.S.C. 154(b) by 0 days.

(21) Appl. No.: 10/471,790

(22) PCT Filed: Mar. 19, 2002

(86) PCT No.: PCT/JP02/02580
§ 371 (c)(1),
(2), (4) Date: Sep. 16, 2003

(87) PCT Pub. No.: WO02/074169
PCT Pub. Date: Sep. 26, 2002

(65) Prior Publication Data
US 2004/0079155 A1 Apr. 29, 2004

(30) Foreign Application Priority Data
Mar. 19, 2001 (JP) .......................... 2001-078999

(51) Int. Cl.$^7$ .............................................. G01N 29/00
(52) U.S. Cl. ............................ 73/573; 73/602; 600/438
(58) Field of Search ....................... 73/602, 573, 629; 600/437, 438

(56) References Cited

U.S. PATENT DOCUMENTS 5,921,929 A  *  7/1999  Goll et al. ................... 600/438
6,308,715 B1 * 10/2001  Weissman et al. ........... 600/437

FOREIGN PATENT DOCUMENTS

| JP | A 3-286751 | 12/1991 |
| JP | A 5-317313 | 12/1993 |
| JP | A 9-84789 | 3/1997 |
| JP | A 9-145691 | 6/1997 |
| JP | A 11-118689 | 4/1999 |

OTHER PUBLICATIONS

Omata, "Measurements of the Hardness of a Soft Material with a Piezoelectric Vibrometer and Their Analysis," Medical Electronics and Bioengineering, vol. 28, No. 1, pp. 1–8, 1990.
Omata et al., "New tactice sensor like the human hand and its applications," Sensors and Actuators A, 35, pp. 9–15, 1992.
Kusaka et al., "Objective Evaluation of Liver Consistency to Estimate Hepatic Fibrosis and Functional Reserve for Hepatectomy" Journal of the American College of Surgeons, vol. 191, No. 1, pp. 47–53, 2000.

* cited by examiner

*Primary Examiner*—John E. Chapman
(74) *Attorney, Agent, or Firm*—Oliff & Berridge, PLC (57) ABSTRACT

The present invention facilitates measurement of characteristic values corresponding to hardness of a material to be measured inside a living body using the response of a vibration transmission characteristic without the need to remove other tissue materials of the living body by dissecting or opening the abdomen of the living body. The present invention includes a sensor (12) made up of a transmitter and a receiver, frequency component analysis section (14) for the incident wave and reflected wave, a frequency/phase difference specification section (15) for comparing the spectral distribution of the incident wave with the spectral distribution of the reflected wave and specifying a phase difference θx, which is a difference between the phase of the incident wave and the phase of the reflected wave at each frequency fx, and a phase difference compensating operation section (16) that inputs the frequency fx and phase difference θx, performs compensating operations using a reference transmission characteristic curve which has been obtained as a reference beforehand and obtains a frequency variation df when the input phase difference θx is reduced to zero, and is characterized in that hardness of the material is calculated from df.

4 Claims, 9 Drawing Sheets

SUBSTANCE CHARACTERISTIC MEASURING METHOD AND SUBSTANCE CHARACTERISTIC MEASURING INSTRUMENT

TECHNICAL FIELD

The present invention relates to a method and apparatus for measuring material characteristics using pulse waves, and more particularly, to a method and apparatus for measuring material characteristics of characteristic values corresponding to hardness of tissue materials in a living body using ultrasonic pulses.

BACKGROUND ART

Figure 7:
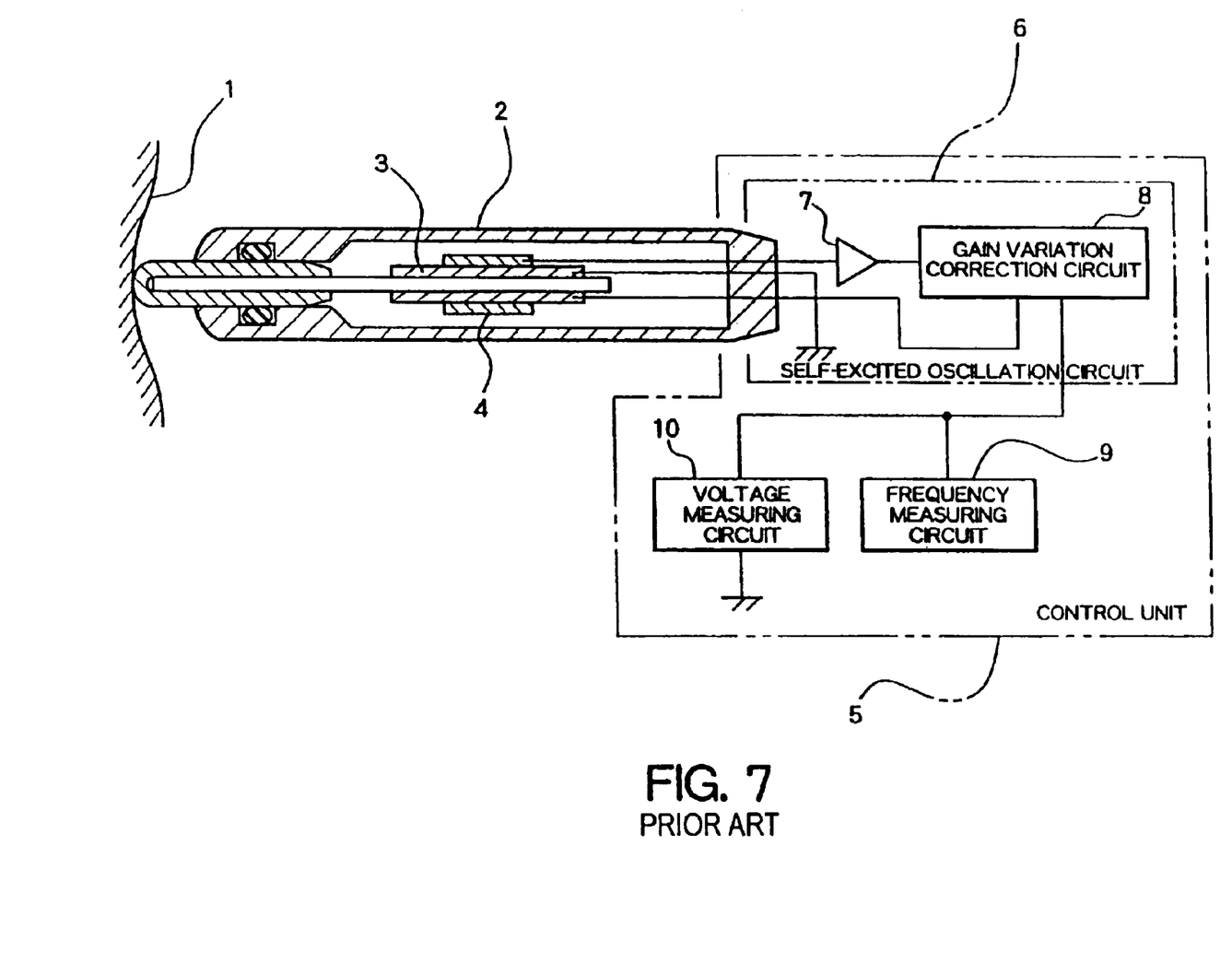
FIG. 7 is a block diagram of an apparatus for measuring the hardness of tissue of a living body according to a conventional example.

One conventional method for measuring the hardness of a tissue material of a living body is a method in which a probe is pressed against the material to be measured, vibration is applied thereto, mechanical vibration response of the tissue material to the input vibration is detected using a sensor, and characteristic values corresponding to the hardness are obtained based on variations in the frequency, phase, etc. Examples of this method are disclosed in, for example, "Measurements of the Hardness of a Soft Material with a Piezoelectric Vibrometer and Their Analysis" (Sadao Omata, Medical Electronics and Bioengineering, Vol. 28, No. 1, 1990, pp1–8) and "New tactile sensor like the human hand and its applications" (S. Omata et al, Sensors and Actuators A, 35 (1992) pp9–15). FIG. 7 shows an apparatus for measuring the hardness of tissue of a living body disclosed in Japanese Patent Laid-Open Publication No. Hei 9-145691. FIG. 7 shows a probe unit 2 pressed against the material 1 to be measured of a living body, for example, the tissue of the skin or the tissue of the viscus, such as a liver tissue exposed when the abdomen is opened. The probe unit 2 includes a vibrator 3 and a strain detection sensor 4, and is connected to an external control unit 5. The control unit 5 has a self-excited oscillation circuit 6 and the self-excited oscillation circuit 6 has an amplifier 7 and a gain variation correction circuit 8. Furthermore, the self-excited oscillation circuit 6 is connected to a frequency measuring circuit 9 to measure its frequency and a voltage measuring circuit 10 to measure its amplitude.

The operation of this conventional example will be explained below. When the probe unit 2 is pressed against the material 1, the vibrator 3 inside the probe unit 2 generates self-excited vibration as an electric signal is converted to mechanical vibration by a mechanical/electrical vibration system of the vibrator 3 and the self-excited oscillation circuit 6 in the control unit 5, and the vibration is input from the end of the probe unit 2 to the material 1. The material 1 responds to this input vibration according to its mechanical vibration transmission characteristic. The strain detection sensor 4 detects this output vibration (strain) and converts it to an electric signal. The vibrator 3 and the strain detection sensor 4 can be implemented by, for example, a piezoelectric vibration element and a piezoelectric sensor. The vibrator 3 and the strain detection sensor 4 together with the amplifier 7 form a feedback loop and then oscillation is self-excited. Here, as a result of the material 1 responding to the input signal from the vibrator 3, generally the frequency changes, a phase difference is generated and the amplitude is reduced. But the gain variation correction circuit 8 has a function of correcting the amplitude gain of the output signal of the strain detection sensor 4. Furthermore, because the gain variation correction circuit 8 is formed in the feedback loop of the self-excited oscillation circuit 6, feedback is provided in such a way that the phase difference generated becomes to zero while the amplitude gain is being corrected. When the phase difference is fed back to zero, the resonance frequency of the mechanical/electrical vibration system, which includes the material 1, the vibrator 3, the self-excited oscillation circuit 6, and the strain detection sensor 4, can be obtained by the frequency measuring circuit 9.

Figure 8:
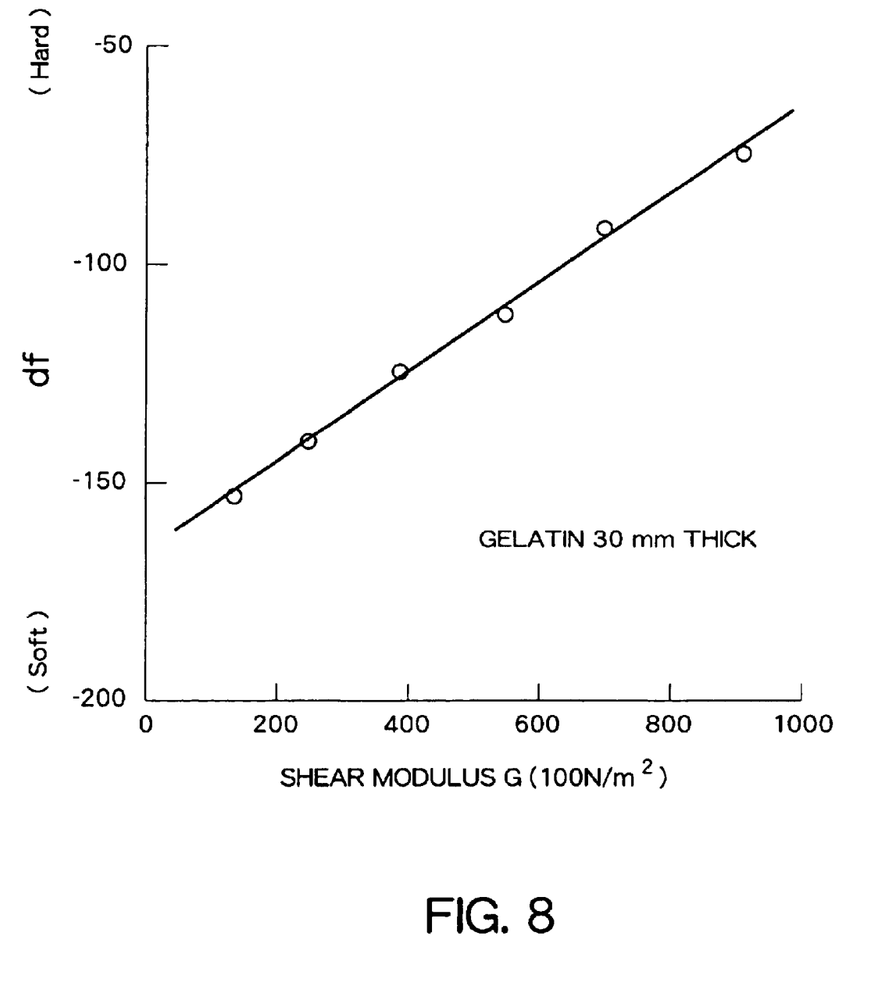
FIG. 8 illustrates an example of a relationship between frequency variation df and the shear modulus G.
Figure 9:
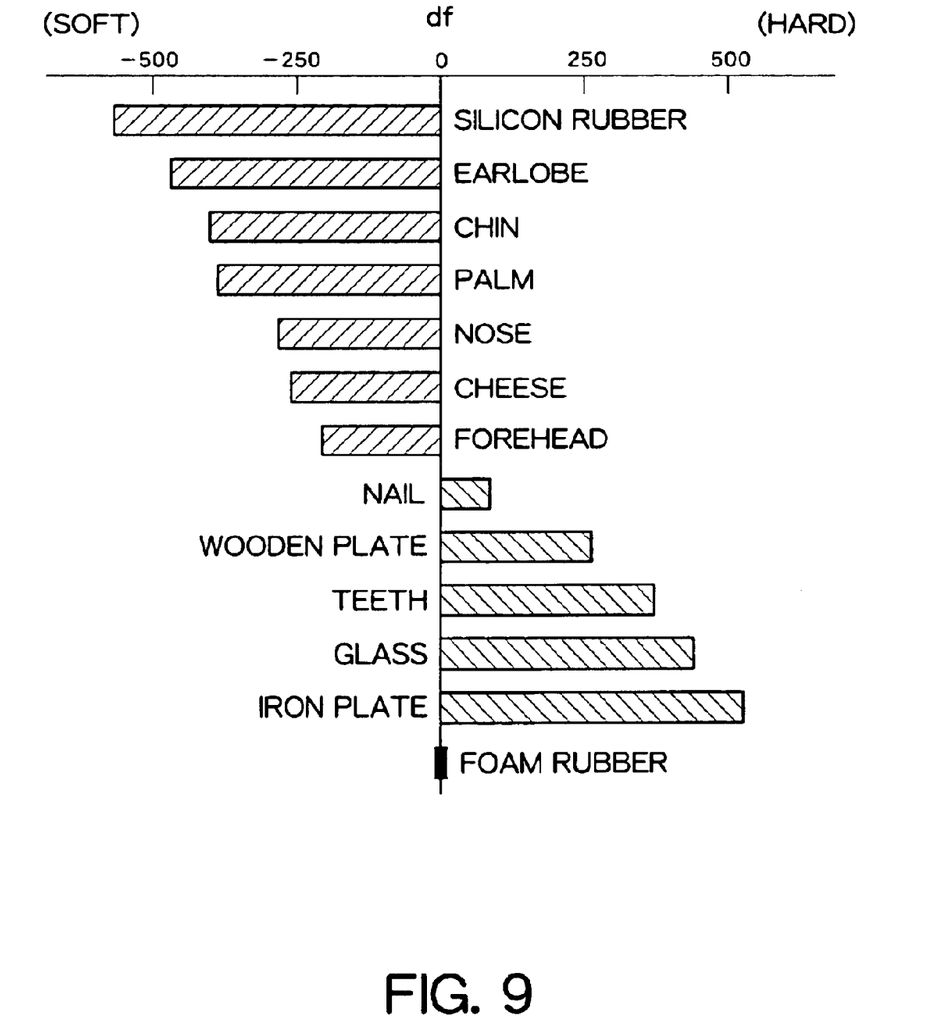
FIG. 9 illustrates values of frequency variations df of various materials.

As is well known, because this resonance state is a speed resonance state, the resonance amplitude reaches its maximum value when the phase is zero, irrespective of the damping constant of the system; this is unlike a displacement resonance state or an acceleration resonance state. Therefore, as irrespective of the damping constant, it is possible to calculate a spring constant of the material by obtaining the resonance frequency when the phase is zero. Therefore, a frequency variation df between this resonance frequency and the frequency when the probe unit 2 is not in contact with the material 1 is the characteristic value corresponding to the hardness of the material 1. For example, FIG. 8 shows a relationship between the frequency variation df and the shear modulus G measured by another method in the case of a gelatin of 30 mm in thickness. FIG. 9 shows values of frequency variation df of various materials containing tissues of a living body using foam rubber as a reference. From the frequency variation df measured in this manner, it is possible to calculate the hardness of the material 1 based on the correlation with the shear modulus G, the correlation with the Young's modulus using a known relational expression and the correlation with spring constant of the material 1 against which a specimen having a certain diameter is pressed.

The apparatus for measuring the hardness of a material in the above-described conventional example uses a response of the material 1 which is excited by the vibrator 3, that is the response of the vibration transmission characteristic, including the spring constant of the material 1, under the speed resonance state. In this manner it is possible to obtain a numerical value for the characteristic value corresponding to the hardness of tissue of a certain living body which is the material 1. However, this configuration requires that the probe unit 2 be directly pressed against the material 1 to provide a signal from the vibrator 3 to the material 1. In other words, to obtain a characteristic value corresponding to the hardness of a tissue material inside a living body, it is necessary to dissect or open the abdomen of the living body, remove other tissue materials of the living body that block access to the material 1, and then directly press the probe unit 2 against the material 1.

The present invention provides a method and an apparatus for measuring material characteristics capable of solving the problems of the above-described conventional technology and easily measuring characteristic values corresponding to the hardness of the material to be measured inside the living body using the response of a vibration transmission characteristic without the need to remove other tissue materials of the living body by dissecting or opening the abdomen of the living body.

DISCLOSURE OF INVENTION

To achieve the above-described advantage, a method for measuring material characteristics according to the present invention includes an incident wave frequency component analysis step of performing a frequency component analysis of a pulse wave introduced into a material to be measured and obtaining frequencies of respective sine wave components and a spectral distribution of phase differences obtained from sine wave components and cosine wave components at those frequencies, a reflected wave frequency component analysis step of performing a frequency component analysis of the wave reflected from the material to which was introduced the incident wave and obtaining frequencies of respective sine wave components and a spectral distribution of phase differences obtained from sine wave components and cosine wave components at those frequencies, and a frequency/phase difference specification step of comparing the spectral distribution of the incident wave with the spectral distribution of the reflected wave and specifying a phase difference θx, which is a difference between the phase of the incident wave and the phase of the reflected wave at each frequency fx, characterized in that a material characteristic value corresponding to the hardness of the material is obtained from values of these fx and θx.

Furthermore, the method for measuring characteristics corresponding to the hardness of a material according to the present invention may be the above-described method for measuring material characteristics further including a phase difference compensating operation step of inputting the above-described frequency fx and phase difference θx, performing operations to compensate the input phase difference θx by using a predetermined reference transmission characteristic curve indicating a relationship between the frequency of the incident wave and an amplitude gain and a phase difference of the reflected wave when vibration at a certain frequency is input, and obtaining a frequency variation df when the input phase difference θx is reduced to zero, characterized in that the hardness of the material is obtained from df.

An apparatus for measuring material characteristics according to the present invention includes pulse inputting means for inputting a pulse wave to a material to be measured, incident wave frequency component analysis means for performing a frequency component analysis of the incident wave and obtaining frequencies of respective sine wave components and a spectral distribution of phase differences obtained from sine wave components and cosine wave components at those frequencies, pulse receiving means for receiving a reflected wave from the material to which was introduced the incident wave, reflected wave frequency component analysis means for performing a frequency component analysis of the reflected wave and obtaining frequencies of respective sine wave components and a spectral distribution of phase differences obtained from sine wave components and cosine wave components at those frequencies, and frequency/phase difference specification means for comparing the spectral distribution of the incident wave with the spectral distribution of the reflected wave and specifying a phase difference θx, which is a difference between the phase of the incident wave and the phase of the reflected wave at each frequency fx, characterized in that a material characteristic value corresponding to the hardness of the material is obtained from values of fx and θx.

Furthermore, the apparatus for measuring characteristics corresponding to the hardness of a material according to the present invention may be the above-described apparatus for measuring material characteristics further including a phase difference compensating operation apparatus for inputting the above-described frequency fx and phase difference θx, performing operations to compensate the input phase difference θx, by using a predetermined reference transmission characteristic curve indicating a relationship between the frequency of the incident wave and an amplitude gain and a phase difference of the reflected wave when vibration at a certain frequency is input, and obtaining a frequency variation df when the input phase difference θx is reduced to zero, characterized in that the hardness of the material is obtained from df.

The method and apparatus for measuring characteristics corresponding to the hardness of a material according to the present invention is constructed in such a manner that a pulse wave is input to a material to be measured from the outside, a wave reflected from the material to be measured is received, a frequency component of the incident wave and the reflected wave are analyzed, the frequencies of the respective sine wave components and the spectral distribution of the phase difference obtained from the sine wave components and cosine wave components at those frequencies are compared, and a phase difference θx, which is a difference between the phase of the incident wave and the phase of the reflected wave at each frequency fx, is specified, as a result of which is thereby obtained a material characteristic value corresponding to the hardness of the material from the values of these fx and θx. Therefore, even if other tissue materials are interposed between the pulse inputting means, the pulse receiving means and the material to be measured, the variations in the characteristic value due to the presence of the other tissue materials of the living body in the round trip of the pulse wave can be canceled out. Because the pulse wave reaches the material to be measured through the other tissue materials and on its return the pulse wave again travels through the same tissue materials. It is therefore possible to measure the characteristics of a material in a living body, without dissecting or opening the body.

Furthermore, the apparatus is also constructed in such a way as to input the frequency fx and the phase difference θx, perform operations to compensate the phase difference θx by using a predetermined reference transmission characteristic curve indicating a relationship between the frequency of the incident wave and an amplitude gain and a phase difference of the reflected wave when vibration at a certain frequency is input, and obtain a frequency variation df when the input phase difference θx is reduced to zero. Because the response of the vibration transmission characteristic including the spring constant of the material to be measured is used, it is possible to obtain a characteristic value corresponding to the hardness of the material to be measured.

BEST MODE FOR CARRYING OUT THE INVENTION

Figure 1:
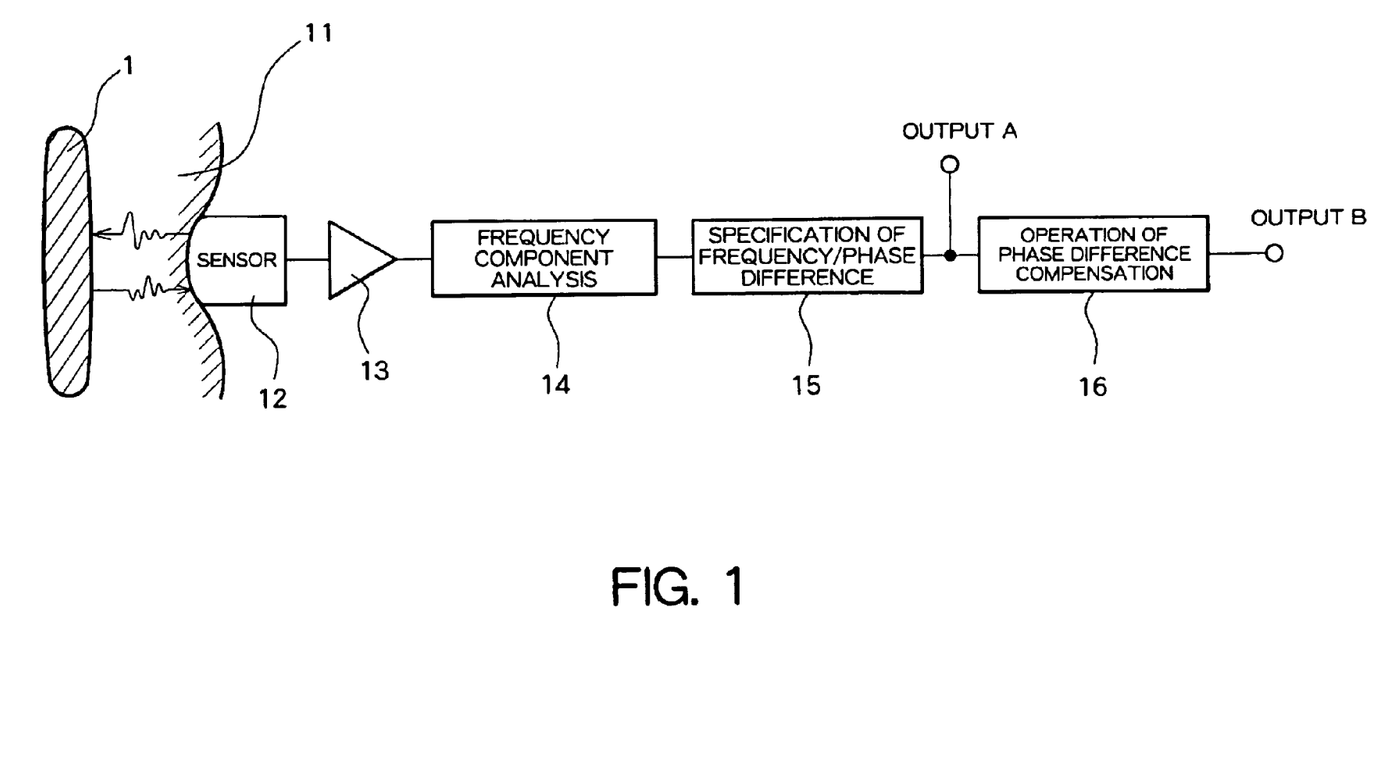
FIG. 1 is a block diagram of a method for measuring characteristics corresponding to the hardness of a material according to an embodiment of the present invention.

With reference now to the attached drawings, a preferred embodiment of the present invention will be explained in detail below. FIG. 1 shows a case where a material 1 to be measured is inside organism tissue in a living body 11. The part denoted as a sensor 12 is an ultrasonic probe which contains an ultrasonic wave input section, a transmitter, that introduces an ultrasonic pulse into an external material and an ultrasonic wave reception section, a receiver, that receives the reflected wave which is reflected from the external material introduced the incident pulse. This sensor 12 is coupled with an amplifier 13, a frequency component analysis section 14, a frequency/phase difference specification section 15 and a phase difference compensating operation section 16 in that order. An output section A is extracted from the result of the frequency/phase difference specification section 15 and an output section B is extracted from the result of the phase difference compensating operation section 16.

Figure 2:
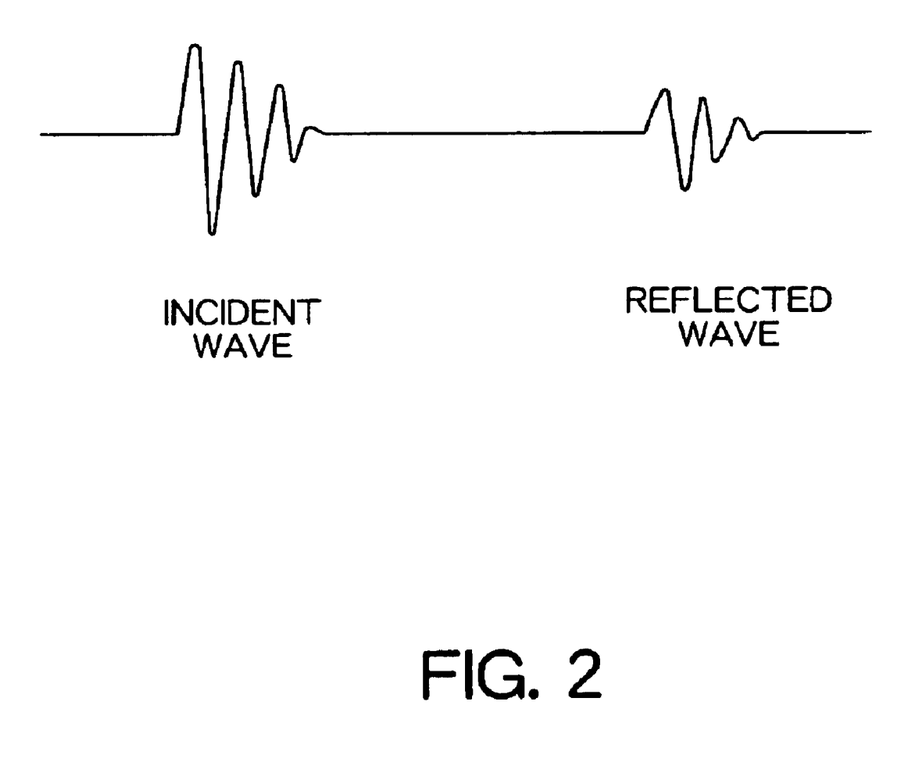
FIG. 2 illustrates pulse waves of an incident wave and a reflected wave according to the embodiment of the present invention using the horizontal axis as the time axis.

An example operation of such a configuration will be explained. When the sensor 12, which is an ultrasonic probe, is pressed against the tissue of the living body 11, an ultrasonic pulse wave is input from an ultrasonic wave input section inside the sensor 12 to the living body 11, propagates inside the tissue, reaches the material 1, is reflected, propagates all the way back through the tissue of the living body 11, its reflected pulse wave is detected by the ultrasonic wave reception section inside the sensor 12 and converted to an electric signal. Various ultrasonic probes are commercially available as the sensor 12, such as one having both functions of the incident section and reception section on a single element or one provided with the incident section and reception section separately. FIG. 2 schematically shows an incident wave and a reflected wave with the horizontal axis indicating the time axis and the vertical axis indicating the amplitude of electric signals of the pulse waves. Generally, the amplitude of the reflected wave is reduced compared to that of the incident wave, and the reflected wave shows changes in the spectra of frequency components, phase difference, etc. These changes reflect the characteristic of the material 1, which may be, for example, a liver. Furthermore, when the incident wave passes through the tissue of the living body 11, is reflected by the liver as the material 1, and returned, the characteristic of the propagation path when the pulse wave is reflected from the surface of the liver, etc., is the same as the characteristic of the incident propagation path to the liver, etc., and therefore the above-described change reflects only the characteristic of the liver, etc., which is the material 1.

Figure 3:
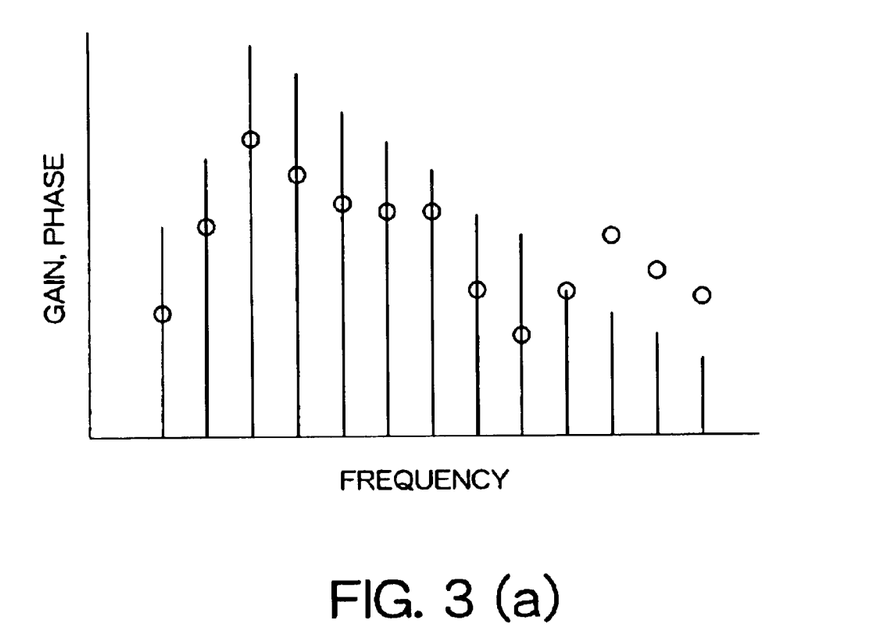
FIG. 3(a) and FIG. 3(b) schematically illustrate examples of a result of a frequency component analysis of the incident wave and reflected wave respectively, according to the embodiment of the present invention.

The signals of these incident wave and reflected wave are amplified by the amplifier 13 to an appropriate signal level, the frequency component analysis section 14, then performs a frequency component analysis of the incident wave and reflected wave and obtains frequencies of the respective sine wave components and a spectral distribution from the sine wave components and the cosine wave components at those frequencies. FIG. 3 schematically shows an example result of such a frequency component analysis. FIG. 3(a) shows the frequency component of the incident wave and FIG. 3(b) shows the frequency component of the reflected wave with the horizontal axis indicating the frequency and the vertical axis indicating the gain and the phase of each frequency component expressed as the length of a solid line in the height direction and the position of the height marked with a circle, respectively. Here, a technique generally called "Fourier analysis" can be used for the frequency component analysis. As is well known, a periodic function of an electric signal can be expanded into a Fourier series, and therefore a pulse wave can be expressed as a set of many sine wave components with different frequencies and amplitudes. Here, the Fourier series is divided into a sine wave component and a cosine wave component at the same frequency and these components are combined and expressed as a single sine wave component having a phase difference at that frequency. Therefore, the phase difference here refers to a phase difference calculated from the sine wave component and cosine wave component at that frequency.

Figure 4:
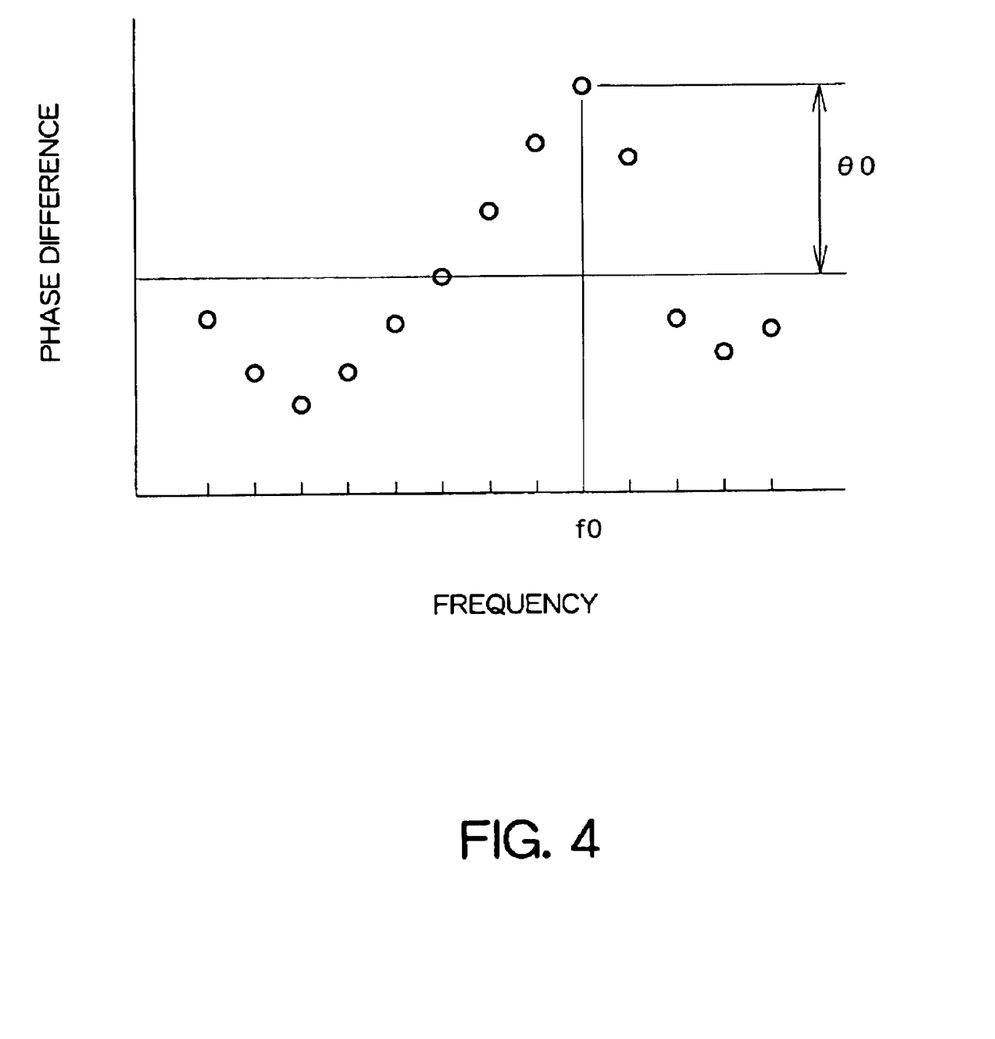
FIG. 4 schematically illustrates an example of a result of specification of a frequency/phase difference according to the embodiment of the present invention.

Then, the frequency/phase difference specification section 15 compares the spectral distribution of the above-described incident wave with the spectral distribution of the above-described reflected wave, calculates and specifies a phase difference θx which is a difference between the phase of the incident wave and the phase of the reflected wave at each frequency fx. FIG. 4 shows an example of identification of the frequency and the phase difference obtained from FIG. 3(a) and FIG. 3(b). Although the identification of such a frequency/phase difference may be done through manual operation, because an enormous amount of data must be processed, it is preferable to use a high-speed digital signal processor (DSP). The data combining the frequency fx and the phase difference θx in the identification of the frequency/phase difference reflects a material characteristic corresponding to hardness of the material 1, and therefore this value is extracted from the output section A and used.

The data of this one set of the identified frequency and phase difference is obtained by a single measurement. A set of the frequency and phase difference corresponding to a frequency component with the largest phase difference will be considered. For example, according to the data for the specification of the frequency/phase difference in FIG. 4, the component indicated by f0 and θ0 in FIG. 4 shows the largest change in the phase difference. The set of frequency f0 and phase difference θ0 showing the largest change in the phase difference in particular is considered to represent a characteristic value of the material to be measured. Therefore, the following explanations will focus on the processing of the set of frequency f0 and phase difference θ0 showing the largest change in the phase difference.

Figure 5:
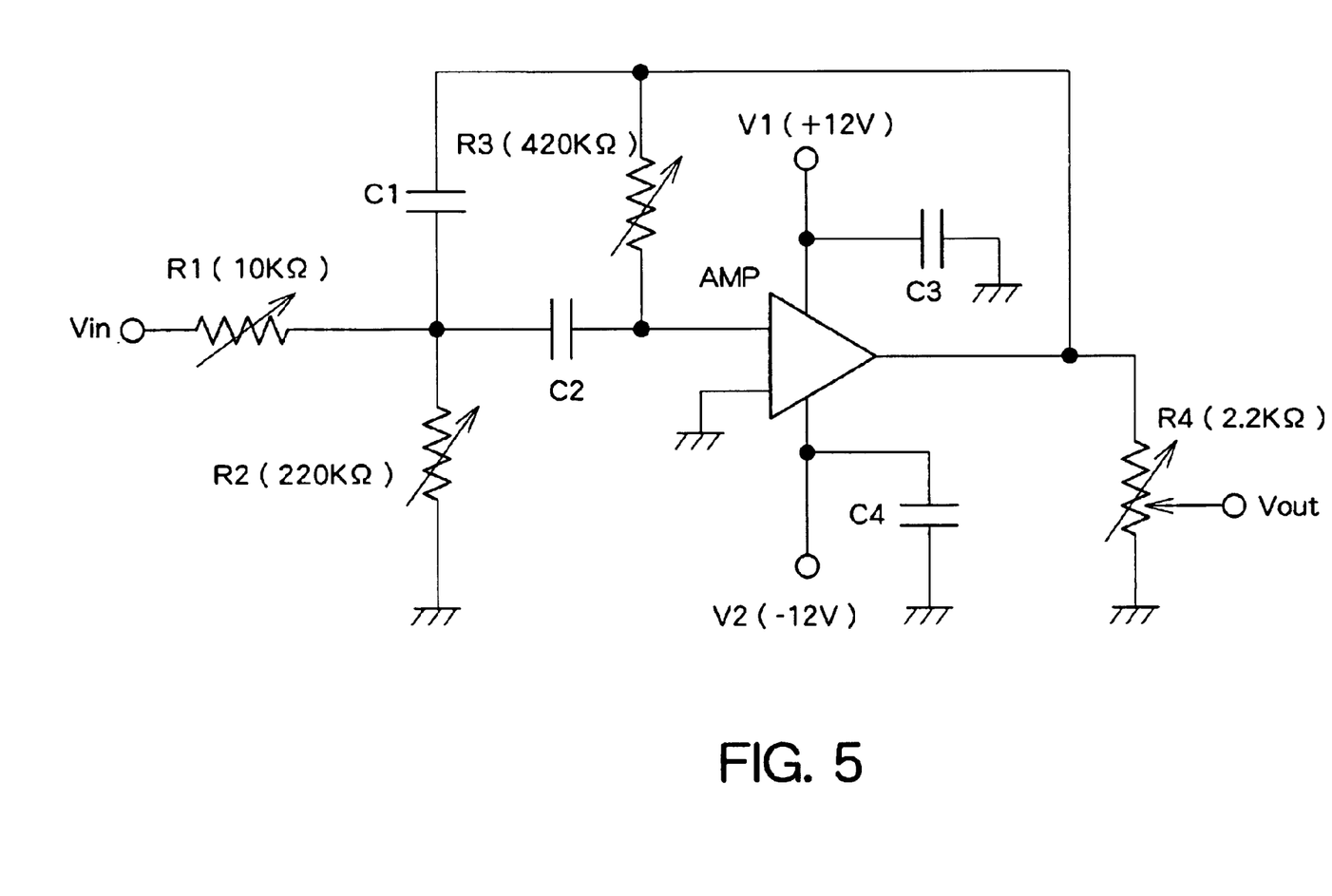
FIG. 5 is a circuit block diagram for realizing a reference transmission characteristic curve according to the embodiment of the present invention.
Figure 6:
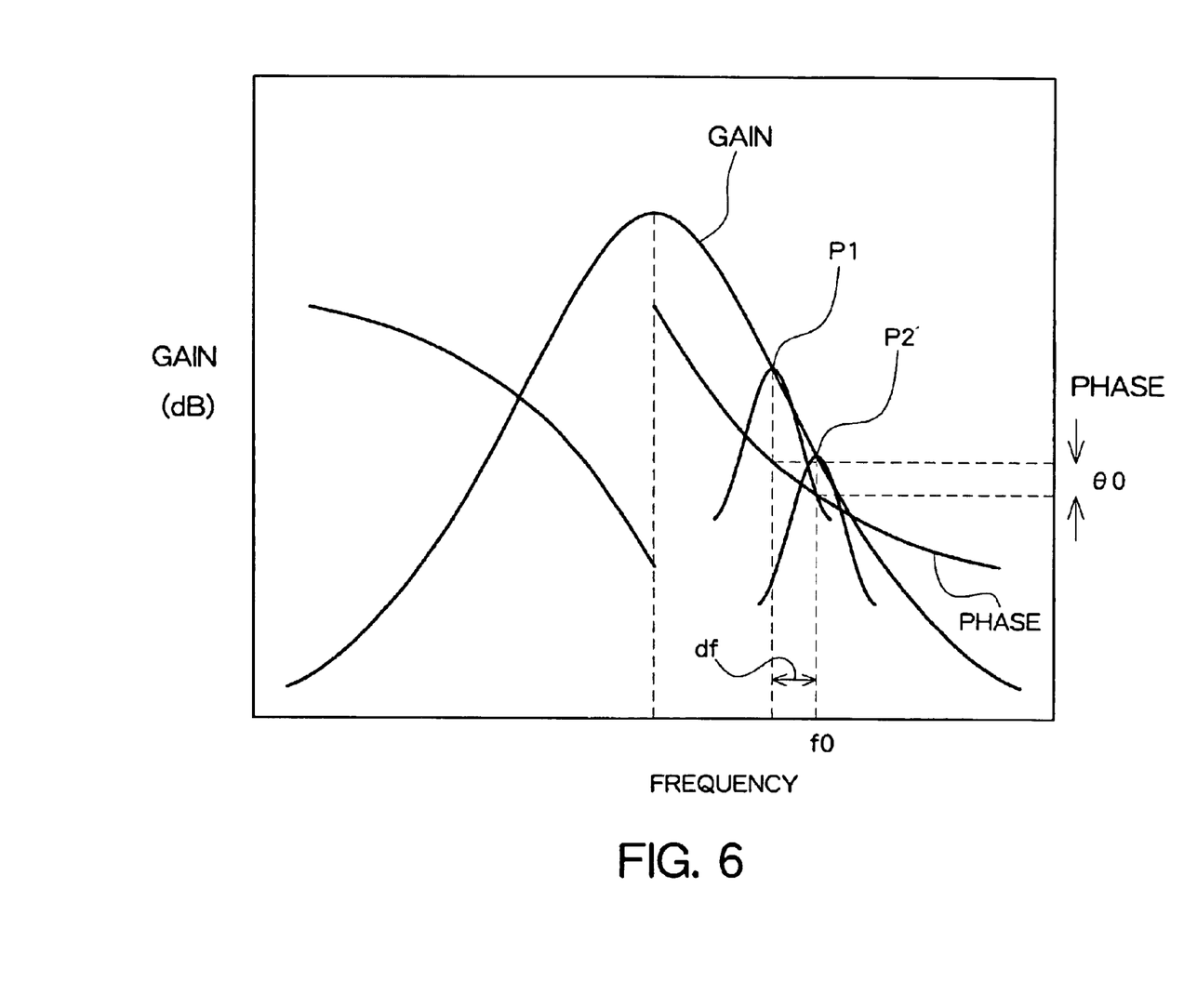
FIG. 6 is a reference transmission characteristic curve according to the embodiment of the present invention.

The phase difference compensating operation section 16 inputs the frequency f0 and the phase difference θ0, performs compensating operations using a vibration transmission characteristic curve, predetermined as a reference, indicating a relationship between the frequency of the incident wave and the amplitude gain and the phase difference of the reflected wave when vibration at a certain frequency is input, and obtains a frequency variation df when the input phase difference θ0 is set to zero. In consideration of the fact that, in a speed resonance characteristic of a vibration system with a single degree of freedom, the frequency increases and amplitude decreases as stiffness (hardness) increases, whereas the frequency decreases and amplitude increases as stiffness (hardness) decreases, it is desirable to have a characteristic of a low pass filter or band pass filter whose amplitude reaches a maximum at a resonance frequency. Such a filter characteristic can also be obtained with the circuit configuration shown in FIG. 5. Furthermore, the filter characteristic in such a circuit configuration can also be implemented as software for performing appropriate calculations. FIG. 6 shows an example of a band pass filter characteristic whose amplitude gain reaches a maximum at a resonance frequency on such a reference transmission characteristic curve. The horizontal axis shows the frequency and the vertical axis shows the amplitude gain and the phase as relative values. To perform a phase difference compensating operation using the calculation of this transmission characteristic curve, the frequency f0 and phase difference θ0 are obtained on this transmission characteristic curve (P2 in FIG. 6), the portion corresponding to the phase difference θ0 is shifted from the phase difference characteristic curve (P1 in FIG. 6), and a corresponding frequency variation df is obtained. This state corresponds to the case when the phase difference θ0 is reduced to zero. Here, the phase difference θ0 obtained from the output section A is the phase difference calculated from the sine wave component and the cosine wave component using a Fourier analysis, and the value itself is a characteristic value of the material corresponding to its hardness. Going one step further, this frequency variation df is a characteristic value more closely related to the hardness of the material, which is converted through the reference transmission characteristic curve considering stiffness such as spring constant. Therefore the frequency variation df is extracted from the output section B and employed in subsequent calculations.

Moreover, instead of calculating the above-described reference transmission characteristic curve, it is also possible to calculate a transmission characteristic curve regarding a well known material, such as ordinary human fat. In such a case, it is possible to express the frequency variation df including human individual differences, body regional differences, etc., by using the stiffness of the ordinary human fat as a reference. It is also possible to collect the frequency variation df regarding a representative tissue of a living body or a standard material (a foam rubber or a gelatin that is close to a living body) whose stiffness can be directly obtained using a different method, and obtain calibration curves of frequency variation df and the stiffness. And thereby it is possible to obtain the stiffness using this calibration curves. In these cases, the stiffness of a material can be obtained as a characteristic value using the standard material as a reference.

Furthermore, the sensor 12 is not limited to one having a single set of the functions of the incident section and reception section, but a plurality of sets can also be provided. When a plurality of sets are provided, it is possible to measure a wider area of the material simultaneously as a two dimensional distribution.

What is claimed is:

1. A method for measuring material characteristics comprising:

an incident wave frequency component analysis step of performing a frequency component analysis of a pulse wave introduced into a material to be measured and obtaining frequencies of respective sine wave components and a spectral distribution of phase differences obtained from sine wave components and cosine wave components at those frequencies;

a reflected wave frequency component analysis step of performing a frequency component analysis of a wave reflected from the material to which was introduced the incident wave and obtaining frequencies of respective sine wave components and a spectral distribution of phase differences obtained from sine wave components and cosine wave components at those frequencies; and a frequency/phase difference specification step of comparing the spectral distribution of the incident wave with the spectral distribution of the reflected wave and specifying a phase difference θx, which is a difference between the phase of the incident wave and the phase of the reflected wave at each frequency fx, and determining about a maximum change in the phase difference, wherein a characteristic value of the material corresponding to the hardness of the material is obtained from values of fx and θx.

2. The method for measuring material characteristics according to claim 1, further comprising a phase difference compensating operation step of inputting the frequency fx and the phase difference θx, performing operation to compensate the phase difference θx by using a predetermined reference transmission characteristic curve indicating a relationship between the frequency of the incident wave and an amplitude gain and a phase difference of the reflected wave when vibration at a certain frequency is input, and obtaining a frequency variation df when the input phase difference θx is reduced to zero, wherein the hardness of the material is obtained from df.

3. An apparatus for measuring material characteristics comprising:

pulse inputting means for inputting a pulse wave to a material to be measured;

incident wave frequency component analysis means for performing a frequency component analysis of the incident wave and obtaining frequencies of respective sine wave components and a spectral distribution of phase differences obtained from sine wave components and cosine wave components at those frequencies;

pulse receiving means for receiving a reflected wave from the material which was introduced the incident wave;

reflected wave frequency component analysis means for performing a frequency component analysis of a wave reflected and obtaining frequencies of respective sine wave components and a spectral distribution of phase differences obtained from sine wave components and cosine wave components at those frequencies; and frequency/phase difference specification means for comparing the spectral distribution of the incident wave with the spectral distribution of the reflected wave and specifying a phase difference θx, which is a difference between the phase of the incident wave and the phase of the reflected wave at each frequency fx, and for determining about a maximum change in the phase difference, wherein a material characteristic value corresponding to the hardness of the material is obtained from values of these fx and θx.

4. The apparatus for measuring material characteristics according to claim 3, further comprising a phase difference compensating operation apparatus for inputting the frequency fx and the phase difference θx, performing operations to compensate the phase difference θx by using a predetermined reference transmission characteristic curve indicating a relationship between the frequency of the incident wave and an amplitude gain and a phase difference of the reflected wave when vibration at a certain frequency is input, and obtaining a frequency variation df when the input phase difference θx is reduced to zero, wherein the hardness of the material is obtained from df.

* * * * *